(12) United States Patent
Baenteli et al.

(10) Patent No.: US 7,666,877 B2
(45) Date of Patent: Feb. 23, 2010

(54) ERGOLINE DERIVATIVES

(75) Inventors: Rolf Baenteli, Basel (CH); Fraser Glickman, Basel (CH); Jiri Kovarik, Zürich (CH); Ian Lewis, Riehen (CH); Markus Streiff, Birsfelden (CH); Gebhard Thoma, Lörrach (DE); Hans-Günter Zerwes, Lörrach (DE)

(73) Assignee: Novartis AG, Basel (CH)

( * ) Notice: Subject to any disclaimer, the term of this patent is extended or adjusted under 35 U.S.C. 154(b) by 10 days.

(21) Appl. No.: 11/914,570

(22) PCT Filed: May 29, 2006

(86) PCT No.: PCT/EP2006/005106

§ 371 (c)(1),
(2), (4) Date: Nov. 16, 2007

(87) PCT Pub. No.: WO2006/128658

PCT Pub. Date: Dec. 7, 2006

(65) Prior Publication Data

US 2009/0018127 A1    Jan. 15, 2009

(30) Foreign Application Priority Data

May 31, 2005    (GB) .................................... 0511060

(51) Int. Cl.
*A61K 31/48* (2006.01)
*C07D 457/08* (2006.01)
(52) U.S. Cl. ................ 514/288; 546/69; 544/60; 544/361; 514/228.2; 514/253
(58) Field of Classification Search ............ 514/288, 514/228.2, 253; 546/69; 544/60, 361
See application file for complete search history.

(56) References Cited

FOREIGN PATENT DOCUMENTS

WO    00/42071    7/2000

OTHER PUBLICATIONS

Nakahara, Yuji et al., Database CA [Online] Chemical Abstracts Service, Columbus, Ohio, "Lysergic acid diethylamide and related compounds. I. Synthesis of d-N6-demethyllysergic acid diethylamide", XP002402827, Database accession No. 1972-34449 the abstract. the compound with the Registry-No. [35779-42-1] & Chemical & Pharmaceutical Bulletin 19 (11), pp. 2337-2341, Coden: CPBTAL; Issn: 0009-2363, (1971).

*Primary Examiner*—Charanjit S Aulakh
(74) *Attorney, Agent, or Firm*—Hoxie & Associates LLC

(57) ABSTRACT

Disclosed are ergoline derivatives, Formula (I), wherein either each of $R_1$ and $R_2$, independently, is H; optionally $R_{10}$ and/or $R_{11}$-substituted-phenyl or -phenyl-$C_{1-4}$alkyl; optionally $R_{10}$ and/or $R_{11}$-substituted-heteroaryl or -heteroaryl-$C_{1-4}$ alkyl; optionally $R_{10}$ and/or $R_{11}$-substituted heteroaryl N-oxide; optionally $R_{10}$-substituted $C_1$-$C_8$ alkyl; optionally $R_{10}$-substituted $C_2$-$C_8$ alkenyl, optionally $R_{10}$-substituted $C_2$-$C_8$ alkynyl; optionally $R_{10}$-substituted $C_3$-$C_8$ cycloalkyl, or optionally $R_{10}$-substituted $C_4$-$C_8$ cycloalkenyl; or $R_1$ and $R_2$ form together with the nitrogen atom to which they are attached an optionally $R_{10}$-substituted 3-8 membered ring containing in addition to the nitrogen atom up to 2 heteroatoms selected independently from N, O and S; $R_3$ is H; $OR_1$; $CH_2R_1R_2$; $(CH_2)_{1-2}NR_1R_2$; $CH_2$—$CH_2$—$OR_1$; $CH_2$—$CO$—$NR_1R_2$; or $CO$—$CH_2R_1R_2$; $R_4$ is F; Cl; Br; I; $OR_1$; $NR_1R_2$ or has one of the significances given for $R_1$; and $R_5$ has one of the significances given for $R_1$, in free form or in salt form for preventing or treating disorders or diseases mediated by interactions between chemokine receptors and their ligands.

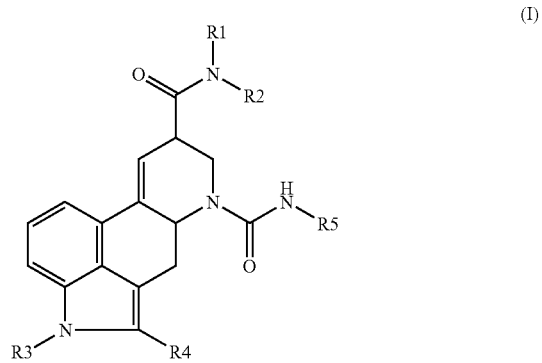

4 Claims, No Drawings

ERGOLINE DERIVATIVES

The present invention relates to ergoline derivatives, a process for their production, their uses as a pharmaceutical, and pharmaceutical compositions containing them.

More particularly, the present invention provides a compound of formula I

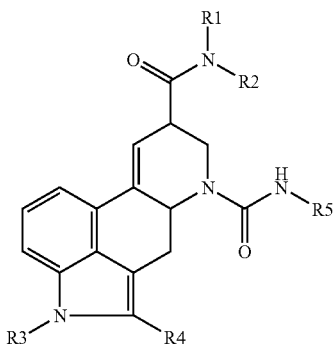

wherein
either each of $R_1$ and $R_2$, independently, is H; optionally $R_{10}$ and/or $R_{11}$-substituted-phenyl or -phenyl-$C_{1-4}$alkyl; optionally $R_{10}$ and/or $R_{11}$-substituted-heteroaryl or -heteroaryl-$C_{1-4}$alkyl; optionally $R_{10}$ and/or $R_{11}$-substituted heteroaryl N-oxide; optionally $R_{10}$-substituted $C_1$-$C_8$ alkyl; optionally $R_{10}$-substituted $C_2$-$C_8$ alkenyl, optionally $R_{10}$-substituted $C_2$-$C_8$ alkynyl; optionally $R_{10}$-substituted $C_3$-$C_8$ cycloalkyl, or optionally $R_{10}$-substituted $C_4$-$C_8$ cycloalkenyl;

or $R_1$ and $R_2$ form together with the nitrogen atom to which they are attached an optionally $R_{10}$-substituted 3-8 membered ring containing in addition to the nitrogen atom up to 2 heteroatoms selected independently from N, O and S;

wherein $R_{10}$ represents 1 to 4 substituents independently selected from $C_1$-$C_6$ alkyl; $C_1$-$C_6$ hydroxyalkyl; $C_1$-$C_6$ alkoxyalkyl; $C_1$-$C_6$ halogenoalkyl; $C_3$-$C_6$ cycloalkyl; $C_2$-$C_6$ alkenyl; $C_3$-$C_6$ cycloalkenyl; $C_2$-$C_6$ alkynyl; phenyl; heteroaryl; heteroaryl N-oxide; F; Cl; Br; I; OH; $OR_9$; $OCOR_9$; $OCOOR_9$; $OCONHR_9$; $OCONR_9R_9$; $OSO_2R_9$; $COR_9$; COOH; $COOR_9$; $CONH_2$; $CONHR_9$; $CONR_9R_9$; $CF_3$; $CHF_2$; $CH_2F$; $C_{1-4}$alkyl$NH_2$; $C_{1-4}$alkyl$NHR_9$; $C_{1-4}$alkyl$NR_9R_9$; CN; $NO_2$; $NH_2$; $NHR_9$; $NR_9R_9$; $NHCOR_9$; $NR_9COR_9$; $NHCONHR_9$; $NHCONH_2$; $NR_9CONHR_9$; $NR_9CONR_9R_9$; $NHCOOR_9$; $NR_9COOR_9$; $NHSO_2R_9$; $N(SO_2R_9)_2$; $NR_9SO_2R_9$; $SR_9$; $SOR_9$; $SO_2R_9$; $SO_2NH_2$; $SO_2NHR_9$; $SO_2NR_9R_9$; or $R_{10}$ is =O attached to a carbon atom of phenyl or heteroaryl or may be one or two =O attached to the same S atom of heteroaryl, if any;

$R_{11}$ represents two adjacent substituents which form an annulated 4-7 membered nonaromatic ring optionally containing up to two heteroatoms selected independently from N, O and S;

each $R_9$, independently, is $C_1$-$C_6$alkyl; hydroxyl-$C_1$-$C_6$alkyl; $C_3$-$C_6$cycloalkyl; $C_2$-$C_6$alkenyl; $C_2$-$C_6$alkynyl; phenyl; benzyl; heteroaryl; —$CH_2$-heteroaryl; or $CF_3$; or two $R_9$, together with the N-atom to which they are attached, form an optionally $R_{10}$-substituted 4-8 membered ring containing in addition to the N-atom up to 2 heteroatoms selected independently from N, O and S;

$R_3$ is H; $OR_1$; $CH_2R_1R_2$; $(CH_2)_{1-2}NR_1R_2$; $CH_2$—$CH_2$—$OR_1$; $CH_2$—CO—$NR_1R_2$; or CO—$CH_2R_1R_2$;

$R_4$ is F; Cl; Br; I; $OR_1$; $NR_1R_2$ or has one of the significances given for $R_1$; and $R_5$ has one of the significances given for $R_1$, In free form or in salt form.

Any alkyl, alkenyl or alkynyl may be linear or branched.

By heteroaryl is meant an aromatic ring system comprising mono-, bi- or tricyclic systems which contains up to 4 heteroatoms independently selected from N, O and S, such as for example furyl, thienyl, pyrrolyl, imidazolyl, pyrazolyl, thiazolyl, isothiazolyl, oxazolyl, isoxazolyl, oxadiazolyl, thiadiazolyl, triazolyl, tetrazolyl, pyridyl, pyridazinyl, pyrimidinyl, pyrazinyl, triazinyl, tetrazinyl, indolyl, benzothiophenyl, benzofuranyl, benzimidazolyl, indazolyl, benzotriazolyl, benzothiazolyl, benzoxazolyl, quinolinyl, isoquinolinyl, phthalazinyl, quinoxalinyl, quinazolinyl, cinnolinyl or naphthyridinyl.

Preferred annulated 4-7membered non-aromatic ring as represented by $R_{11}$ is an annulated 5 or 6 membered non aromatic ring optionally containing 1 or 2 oxygen and includes e.g. —O—$CH_2$—O— or —O—$CH_2$—$CH_2$—O—, attached to 2 adjacent carbon atoms.

The compounds of formula I may exist in free form or in salt form, e.g. addition salts with e.g. organic or inorganic acids, for example, hydrochloric acid, acetic acid when $R_1$, $R_2$, and/or $R_3$ comprises an optionally substituted amino group or a heterocyclic residue which can form addition salts. When the compounds of formula I have one or more asymmetric centers in the molecule, e.g. when a piperidine ring is substituted, the present invention is to be understood as embracing the various optical isomers, as well as racemates, diastereoisomers and mixtures thereof.

In the compounds of formula I, the following significances are preferred individually or in any sub-combination:

1. Each of $R_1$ and $R_2$, independently, is H; optionally $R_{10}$-substituted phenyl; optionally $R_{10}$-substituted heteroaryl; optionally $R_{10}$-substituted heteroaryl N-oxide; optionally $R_{10}$-substituted $C_1$-$C_6$ alkyl; optionally $R_{10}$-substituted $C_2$-$C_6$ alkenyl, optionally $R_{10}$-substituted $C_2$-$C_6$ alkynyl; optionally $R_{10}$-substituted $C_3$-$C_8$ cycloalkyl, or optionally $R_{10}$-substituted $C_4$-$C_8$ cycloalkenyl;

2. $R_1$ and $R_2$ form together with the N-atom to which they are attached an optionally $R_{10}$-substituted 3-6 membered ring containing in addition to the N-atom up to 1 heteroatom selected independently from N, O and S. Preferably, such optionally $R_{10}$-substituted 3-6 membered ring only contains one N atom or two N atoms or one N atom and one O atom; more preferably it is non-aromatic. Examples are e.g. rings derived from optionally $R_{10}$-substituted azetidine, pyrroline, pyrrolidine, piperidine, piperazine, ketopiperazine, thiazine, thiazine-dioxide, tetrahydro-pyridine, piperidone, morpholino or azepine. Preferably such ring is substituted by one or two OH, $C_{1-4}$alkyl, $C_{1-4}$alkoxy, CO—$C_{1-4}$alkyl or carbamoyl;

3. $R_{10}$ represents 1 to 3 substituents independently selected from $C_1$-$C_3$ alkyl; $C_1$-$C_3$ hydroxyalkyl; $C_1$-$C_6$ alkoxyalkyl; $C_1$-$C_3$ halogenoalkyl; phenyl; heteroaryl; F; Cl; OH;

4. $R_3$ is H; $OR_1$; —$CH_2$—$CH_2$—$NR_1R_2$; —$CH_2$—$CH_2$—$OR_1$; —$CH_2$—C(O)—$NR_1R_2$;

5. $R_4$ is F; Cl; Br; I; —$OR_1$; —$NR_1R_2$ or has one of the significances given for $R_1$;

6. $R_5$ has one of the significances given for $R_1$.

The present invention also includes a process for the preparation of a compound of formula I, which process comprises a) for the preparation of a compound of formula I wherein each of $R_3$ and $R_4$ is H, reacting a compound of formula II

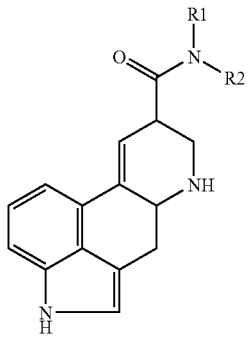

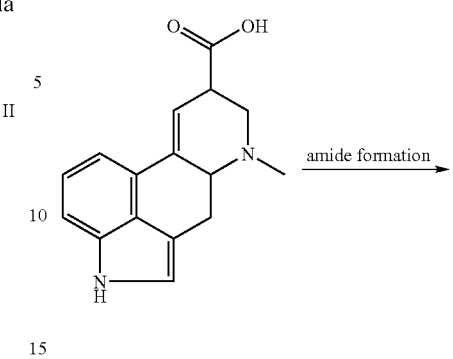

wherein $R_1$ and $R_2$ are as defined above,
with an urea forming agent; or b) for the preparation of a compound of formula I wherein each of $R_3$ and $R_4$ is H, amidating a compound of formula III

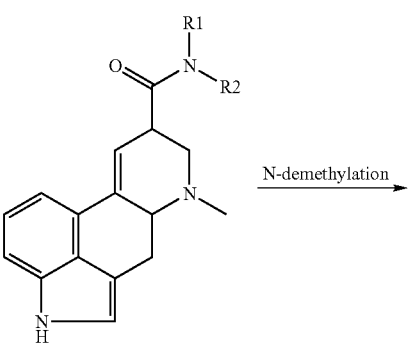

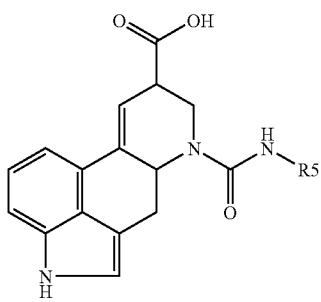

wherein $R_5$ is as defined above, or a functional derivative thereof; or c) for the preparation of a compound of formula I wherein each of $R_3$ and $R_4$ is other than H, converting a compound of formula I wherein each of $R_3$ and $R_4$ is H;

and, where required, converting the resulting compound of formula I obtained in free form into the desired salt form, or vice versa.

The urea forming agent used in process step a) may be e.g. phosgene, triphosgene or trichloromethylformate, followed by addition of an amine. Urea formation may also be obtained when the compound of formula II is reacted with isocyanate.

Amidation in process step b) may conveniently be performed by forming an activated carboxy functional derivative, e.g. acid chloride, mixed anhydride or symmetrical anhydride, followed by reaction with an amine or by direct reaction of e.g. a methyl ester with an amine under heating or with microwave irradiation.

Compounds of formula II, used as starting materials, may be prepared as follows:

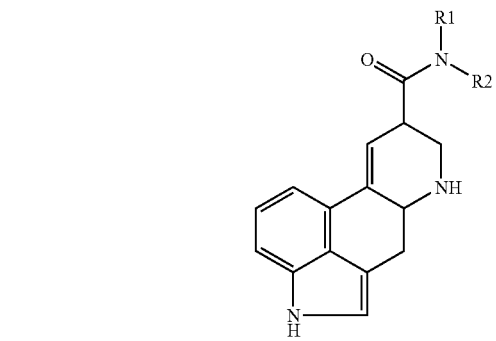

$R_1$ and $R_2$ being as defined above.

Compounds of formula III, used as starting materials, may be prepared as follows:

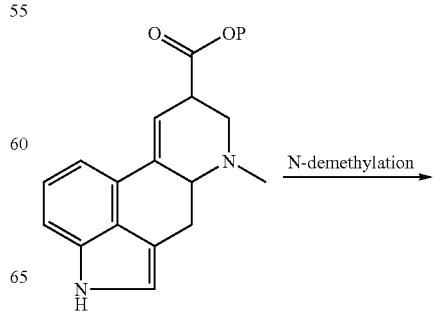

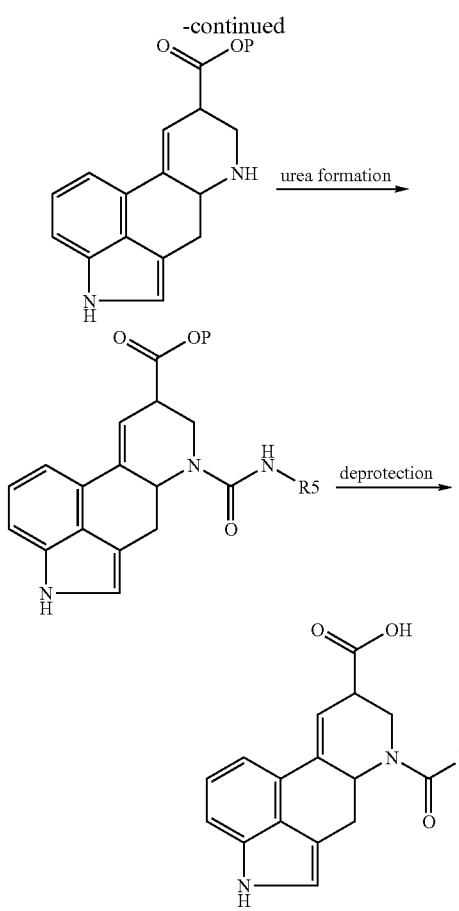

wherein $R_5$ is as defined above and P is a protecting group, e.g. methyl, ethyl, t-butyl, trityl, benzyl, fluorenyl, trimethylsilylethyl or allyl ester.

Above reactions may be carried out in accordance with methods known in the art or as disclosed hereafter. Removal of the protecting group P may be carried out by acid or basic hydrolysis, treatment with fluoride ion or by hydrogenation.

Insofar as the production of the starting materials is not particularly described, the compounds are known or may be prepared analogously to methods known in the art or as described hereafter.

The following Examples are illustrative of the invention, without limitation.

EXAMPLE 1

(6aR,9R)-6,6a,8,9-Tetrahydro-4H-indolo[4,3-fg]quinoline-7,9-dicarboxylic acid 9-diethylamide 7-phenylamide A mixture of the mesylate of (6aR,9R)-4,6,6a,7,8,9-Hexahydro-indolo[4,3-fg]quinoline-9-carboxylic acid diethylamide (122 mg, 0.30 mmol) and isocyanato-benzene (36 mg, 0.30 mmol) in acetone (5 ml) is stirred for 3 h at 25° C. The solvent is removed, and the residue subjected to flash chromatography (SiO$_2$, cyclolhexane/t-butyl methylether 1:0→2:3) to give the title compound. MS/ES: 429 [M+H]$^+$ The compounds of formula

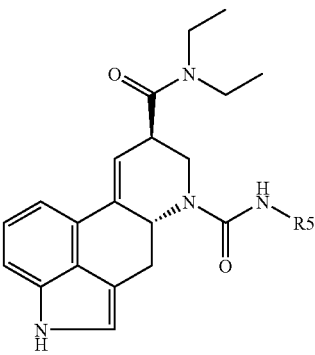

wherein $R_5$ has the significances given in Table 1, are prepared according to a similar procedure.

TABLE I

| Ex. | $R_5$ | MS (ES$^+$) |
|---|---|---|
| 2 | 4-pyridyl | 430 |
| 3 | 3-pyridyl | 430 |
| 4 | 2-pyridyl | 430 |
| 5 | cyclohexyl | 435 |
| 6 | 3-methylphenyl | 443 |
| 7 | 2-methylphenyl | 443 |
| 8 | 4-methylphenyl | 443 |
| 9 | 2-fluorophenyl | 447 |
| 10 | 4-dimethylaminophenyl | 472 |

TABLE I-continued

| Ex. | R$_5$ | MS (ES$^+$) |
|---|---|---|
| 11 | 4-biphenyl group | 505 |
| 12 | 3,4,5-trimethoxyphenyl group | 519 |

EXAMPLE 13

(6aR,9R)-9-(Pyrrolidine-1-carbonyl)-6,6a,8,9-tetrahydro-4H-indolo[4,3-fg]quinoline-7-carboxylic acid phenylamide Step 1: (6aR,9R)-7-Cyano-4,6,6a,7,8,9-hexahydro-indolo[4,3-fg]quinoline-9-carboxylic acid methyl ester To a 50 ml round-bottom flask containing a solution of lysergic acid methyl ester (1.0 g, 3.54 mmol) in anhydrous dichloromethane (50 ml) is slowly added cyanogen bromide (2.02 g, 19.11 mmol) and the resulting black-coloured reaction mixture is stirred at room temperature for 4 hours by which time TLC in 10% methanol/dichloromethane showed partial conversion of starting material to give two faster-running products. The reaction mixture is left stirring over the weekend and monitored by TLC showing no change. The reaction mixture is then stirred at 50° C. for 4 hours and is then extracted between tartaric acid and dichloromethane. The aqueous phase is re-extracted with dichloromethane (100 ml) and the combined organic phases washed with brine (200 ml), dried over MgSO$_4$, filtered and concentrated in vacuo to give a dark brown (tar-coloured) oil. Purification is carried out by Normal Phase Flash column chromatography (Biotage Flash 40, 90 g cartridge) using 40% ethyl acetate/hexane to achieve separation of the fast-running product which is isolated as a pale yellow solid. The product is crystallized from tert. Butyl methylether and slowly evaporated. The resulting crystallized material is filtered at the pump to give pale yellow crystals.

Step 2: (6aR,9R)-4,6,6a,7,8,9-Hexahydro-indolo[4,3-fg]quinoline-9-carboxylic acid methyl ester To a 100 ml round-bottom flask containing a solution of (6aR,9R)-7-Cyano-4,6,6a,7,8,9-hexahydro-indolo[4,3-fg]quinoline-9-carboxylic acid methyl ester (1.57 g, 5.35 mmol) in acetic acid (20 ml) is added water (4 ml) and zinc (1.5 g). The reaction mixture is refluxed at 100° C. for 3 hours by which time TLC in 20% methanol/DCM showed conversion of starting material to give product as a mixture of diastereomers. The reaction mixture is filtered to remove the zinc and the filter paper is washed thoroughly with water (200 ml) and ethyl acetate (200 ml). The aqueous phase is made basic with the addition of solid sodium hydrogen carbonate. The phases are then extracted and allowed to separate. The aqueous phase is re-extracted with ethyl acetate (2×100 ml) and the combined organic phases washed with brine (200 ml), dried (MgSO$_4$), filtered at the pump and concentrated in vacuo to give a beige coloured foam. Purification is carried out by Normal Phase Flash column chromatography (Biotage Flash 40, 40 g cartridge) using 10% methanol/dichloromethane to achieve separation. Product is isolated as a beige foam.

Step 3: (6aR,9R)-7-Phenylcarbamoyl-4,6,6a,7,8,9-hexahydro-indolo[4,3-fg]quinoline-9-carboxylic acid methyl ester To a 100 ml round-bottom flask containing a solution of (6aR,9R)-4,6,6a,7,8,9-hexahydro-indolo[4,3-fg]quinoline-9-carboxylic acid methyl ester (0.89, 2.98 mmol) in dichloromethane (20 ml) is added phenylisocyanate (0.45 ml, 4.5 mmol, 1.5 eq.). The reaction mixture is stirred at room temperature for 16 hours by which time TLC in 10% methanol/DCM showed conversion of starting material to give product as a mixture of diastereomers. The volatiles are concentrated in vacuo and purified directly using Normal Phase Flash column chromatography (Biotage Flash 40, 90 g cartridge) using 30% ethyl acetate/hexane to isolate the product as a 1:1 diastereomeric mixture.

Step 4: (6aR,9R)-7-Phenylcarbamoyl-4,6,6a,7,8,9-hexahydro-indolo[4,3-fg]quinoline-9-carboxylic acid To a 100 ml round-bottom flask containing (6aR,9R)-7-phenylcarbamoyl-4,6,6a,7,8,9-hexahydro-indolo[4,3-fg]quinoline-9-carboxylic acid methyl ester (0.8 g, 2.06 mmol) is added methanol (12 ml), THF (24 ml) and a solution of lithium hydroxide (247 mg) in water (12 ml). The reaction mixture is stirred at room temperature for 20 minutes by which time TLC in 20% methanol/dichloromethane showed complete conversion of starting material. The colour of the crude reaction mixture has changed from light yellow to a violet red. The volatiles are removed in vacuo (leaving only water) and the aqueous solution made acidic with the addition of 1 M HCl. The resulting beige precipitate is filtered at the pump and the filter cake washed with distilled water (50 ml). The filter cake is then dried in a high vacuum oven at 50° C. for 16 hours providing product.

Step 5: (6aR,9R)-9-(Pyrrolidine-1-carbonyl)-6,6a,8,9-tetrahydro-4H-indolo[4,3-fg]quinoline-7-carboxylic acid phenylamide To a 50 ml round-bottom flask containing a suspension of (6aR,9R)-7-phenylcarbamoyl-4,6,6a,7,8,9-hexahydro-indolo[4,3-fg]quinoline-9-carboxylic acid (0.2 g, 0.54 mmol), PYBOP (0.307 g), dichloromethane (10 ml), pyrrolidine (0.054 ml, 0.64 mmol, 1.2 eq.) and Hünigs base (0.187 ml, 1.07 mmol, 2 eq.) are added. The reaction mixture is stirred for 3 hours at room temperature. Purification is carried out by Normal Phase Flash column chromatography (Biotage Flash 40, 40 g cartridge) using 50% ethyl acetate/hexane as the solvent. (6aR,9R)-9-(Pyrrolidine-1-carbonyl)-6,6a,8,9-tetrahydro-4H-indolo[4,3-fg]quinoline-7-carboxylic acid phenylamide is isolated as a beige solid. MS/ES: 427 (M+H)$^+$ The compounds of formula

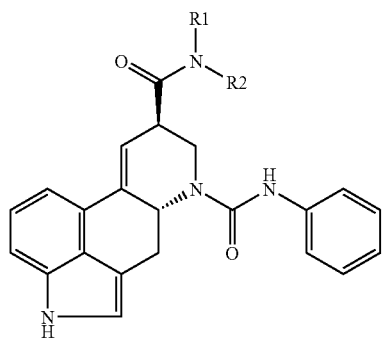

wherein $R_1$ and $R_2$ have the significances given in Table 2, are prepared using similar procedures and the appropriate amines.

TABLE 2

| Ex. | —NR$_1$R$_2$ | MS (ES$^+$) |
| --- | --- | --- |
| 14 | NH$_2$ | 373 |
| 15 | NHEt | 401 |
| 16 | NHPr | 429 |
| 17 | NMe$_2$ | 401 |
| 18 | NEt$_2$ | 429 |
| 19 | N(Me)(allyl) | 427 |
| 20 | N(CH$_2$CH$_2$OMe)$_2$ | 489 |
| 21 | N(Me)(CH$_2$CH$_2$OH) | 431 |
| 22 | N(Me)CH$_2$C(O)NMe$_2$ | 472 |

TABLE 2-continued

| Ex. | —NR$_1$R$_2$ | MS (ES$^+$) |
| --- | --- | --- |
| 23 | azetidinyl | 413 |
| 24 | 2,5-dihydropyrrolyl | 425 |
| 25 | (3S)-3-hydroxypyrrolidinyl | 443 |
| 26 | (3R)-3-hydroxypyrrolidinyl | 443 |
| 27 | (3R,4R)-3,4-dihydroxypyrrolidinyl | 459 |
| 28 | (3S,4S)-3,4-dihydroxypyrrolidinyl | 459 |
| 29 | (3R,4S)-3,4-dihydroxypyrrolidinyl | 459 |
| 30 | (2S)-prolinamide | 470 |
| 31 | (2R)-prolinamide | 470 |
| 32 | piperidinyl | 441 |
| 33 | 1,2,3,6-tetrahydropyridinyl | 439 |
| 34 | azepanyl | 455 |
| 35 | 4-hydroxypiperidinyl | 457 |

TABLE 2-continued

| Ex. | —NR₁R₂ | MS (ES⁺) |
|---|---|---|
| 36 | piperidine with 3,4-diOH | 473 |
| 37 | 4-oxo-piperidine | 455 |
| 38 | thiomorpholine-1,1-dioxide | 491 |
| 39 | piperazine (NH) | 442 |
| 40 | 3-oxo-piperazine | 456 |
| 41 | 4-methyl-piperazine | 456 |
| 42 | 4-acetyl-piperazine | 484 |
| 43 | morpholine | 443 |
| 44 | 2,6-dimethyl-morpholine | 471 |

EXAMPLE 45

(6aR,9R)-9-(Pyrrolidine-1-carbonyl)-6,6a,8,9-tetrahydro-4H-indolo[4,3-fg]quinoline-7-carboxylic acid (2-methoxy-phenyl)-amide Step 1: (6aR,9R)-7-Methyl-4,6,6a,7,8,9-hexahydro-indolo[4,3-fg]quinolin-9-yl)-pyrrolidin-1-yl-methanone 30 g (111.80 mmol) lysergic acid is dissolved in 400 ml dichloromethane and cooled to 0°-5° C., 31.16 ml (223.61, 2 eq.) triethylamine and 18.66 ml (223.61 mmol, 2 eq.) pyrrolidine is added and within 15 minutes 1.5 equivalents propanephosphonic acid anhydride (50% in ethyl acetate). The reaction mixture is stirred for 1 hour at room temperature, then it is poured onto ice and extracted with dichloromethane, the organic layer is dried with Na₂SO₄, evaporated and the residue (28.6 g) is purified by chromatography on silica eluting with dichloromethane:methanol 9:1 to give ((6aR,9R)-7-Methyl-4,6,6a,7,8,9-hexahydro-indolo[4,3-fg]quinolin-9-yl)-pyrrolidin-1-yl-methanone.

Step 2: (6aR,9R)-4,6,6a,7,8,9-Hexahydro-indolo[4,3-fg]quinolin-9-yl-pyrrolidin-1-yl-methanone 6 g (18.67 mmol) of the product of step 1 is dissolved in 180 ml dichloromethane at 0° C. and 5.522 g (22.40 mmol, 1.2 eq.) of 70% meta-chloroperbenzoic acid is added. After 10 minutes the intermediate N-oxide has formed and 2.594 g (9.33 mmol, 0.5 eq.) FeSO4.7H2O in 12 ml methanol is added, the cooling is removed and the mixture is stirred at room temperature. After 1 hour 25 minutes the reaction mixture is extracted with 0.1 M EDTA solution (adjusted to pH 9 beforehand), dried with Na2SO4 evaporated and purified by silica gel chromatography eluting with dichloromethane:methanol:ammonia 93:6:1 to give (6aR,9R)-4,6,6a,7,8,9-Hexahydro-indolo[4,3-fg]quinolin-9-yl-pyrrolidin-1-yl-methanone.

Step 3: (6aR,9R)-9-(Pyrrolidine-1-carbonyl)-6,6a,8,9-tetrahydro-4H-indolo[4,3-fg]quinoline-7-carboxylic acid (2-methoxy-phenyl)-amide 5.087 g (16.54 mmol) of the product of step 2 is dissolved in 80 ml tetrahydrofurane and 1.79 ml (16.5 mmol) 1-isocyanato-2-methoxy-benzene is added and stirred at room temperature. In order to trap excess isocyanate 0.3 equivalent 3-amino-1,2-propanediol is added and stirred for 2.5 hours. Then the reaction mixture is washed with saturated sodium hydrogen carbonate solution and brine, dried with Na₂SO₄ and partially evaporated. Crystallization give (6aR,9R)-9-(Pyrrolidine-1-carbonyl)-6,6a,8,9-tetrahydro-4H-indolo[4,3-fg]quinoline-7-carboxylic acid (2-methoxy-phenyl)-amide. MS/ES: 457 (M+H)⁺

The compounds of formula

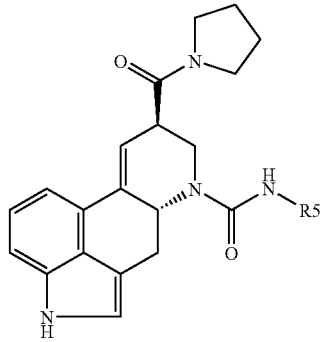

wherein R₅ has the significances given in table 3, are prepared following similar procedures.

TABLE 3

| Ex. | R₅ | MS (M + H)⁺ |
|---|---|---|
| 46 | 3-methoxyphenyl | 457 |

TABLE 3-continued

| Ex. | R₅ | MS (M + H)⁺ |
|---|---|---|
| 47 | 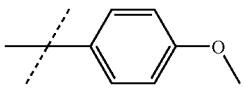 | 457 |
| 48 | 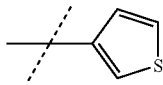 | 433 |
| 49 | 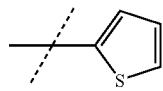 | 433 |
| 50 | 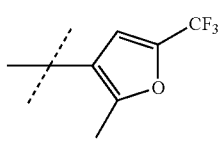 | 499 |
| 51 | 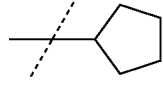 | 419 |
| 52 | 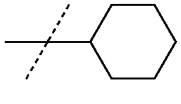 | 433 |
| 53 | 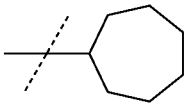 | 447 |
| 54 | 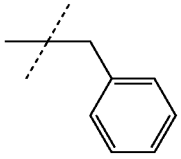 | 441 |
| 55 | 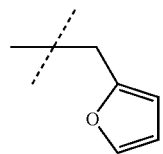 | 431 |

EXAMPLE 56

5-Methyl-9-(piperidine-1-carbonyl)-6,6a,8,9-tetrahydro-4H-indolo[4,3-fg]quinoline-7-carboxylic acid phenylamide 5-Methyl-9-(piperidine-1-carbonyl)-6,6a,8,9-tetrahydro-4H-indolo[4,3-fg]quinoline-7-carboxylic acid phenylamide is prepared following similar procedures as described for Example 45 using 2-methyl-lysergic acid (instead of lysergic acid) and piperidine (instead of pyrrolidine) in step 1 and phenyl isocyanate in step 3. MS: 455 (M+H)⁺

EXAMPLE 57

9-(Pyrrolidine-1-carbonyl)-6,6a,8,9-tetrahydro-4H-indolo[4,3-fg]quinoline-7-carboxylic acid (3-fluorophenyl)-amide 62 mg (0.20 mmol) of the product of step 2 of Example 45 is dissolved in 3 ml of dichloromethane and 0.14 ml (10 eq.) of triethylamine is added and 0.042 ml trichloromethyl chloroformate in 2 ml of dichloromethane. After 30 minutes at room temperature 0.14 ml of triethylamine (10 eq.) and 0.040 ml (2 eq.) of 2-fluoroaniline are added. After stirring for 22 hours at room temperature the reaction mixture is separated between 100 ml dichloro-methane and saturated sodium hydrogen carbonate solution. The organic layer is dried with Na2SO4 and evaporated. The crude product is purified by chromatography on silica gel eluting with ethyl acetate/cyclohexane 3:1 to give 6aR,9R)-9-(Pyrrolidine-1-carbonyl)-6,6a,8,9-tetrahydro-4H-indolo[4,3-fg]quinoline-7-carboxylic acid (3-fluoro-phenyl)-amide. MS/ES: 445 (M+H)⁺

The compounds of formula

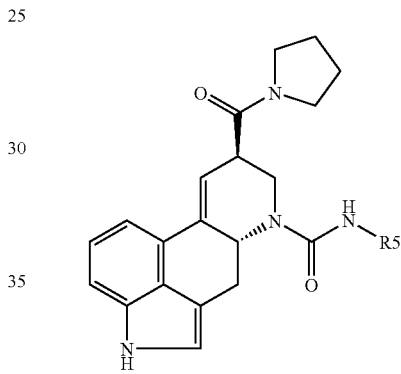

wherein R₅ has the significances given in Table 4, are prepared following similar procedures using appropriate amine reagents.

TABLE 4

| Ex. | R₅ | MS (M + H) | MS (M − H) |
|---|---|---|---|
| 58 | 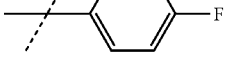 | 445 | 443 |
| 59 | 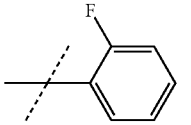 | 445 | 443 |
| 60 | 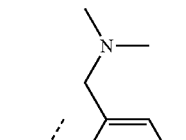 | 484 | 482 |

TABLE 4-continued

| Ex. | R$_5$ | MS (M + H) | MS (M − H) |
|---|---|---|---|
| 61 | 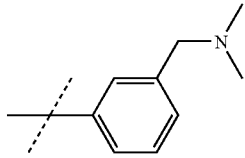 | 484 | |
| 62 | 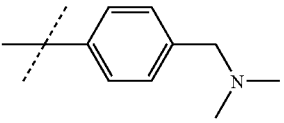 | 484 | 482 |
| 63 | 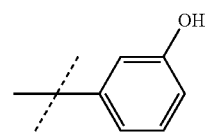 | | 441 |
| 64 | 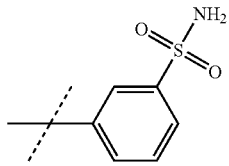 | 506 | 504 |
| 65 | 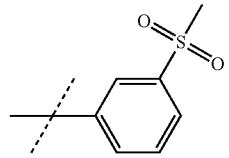 | 505 | |
| 66 | 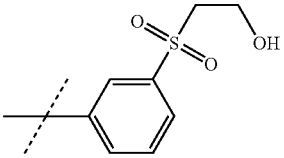 | 535 | 533 |
| 67 | 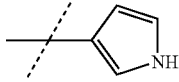 | | 414 |
| 68 | —H | 351 | |
| 69 | —CH$_3$ | 365 | |
| 70 | 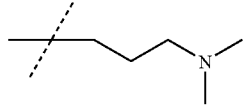 | 436 | |
| 71 | 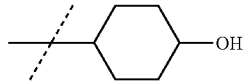 | 449 | |

EXAMPLE 72

(6aR,9R)-5-Chloro-9-(pyrrolidine-1-carbonyl)-6,6a,8,9-tetrahydro-4H-indolo[4,3-fg]quinoline-7-carboxylic acid phenylamide 64 mg of Example 13 (0.15 mmol) is dissolved in 1 ml DMF and 36 mg (0.27 mmol, 1.8 eq.) N-chlorosuccinimid is added and stirred at room temperature. After 55 minutes the reaction mixture is purified by chromatography on silica eluting with ethyl acetate to give (6aR,9R)-5-chloro-9-(pyrrolidine-1-carbonyl)-6,6a,8,9-tetrahydro-4H-indolo[4,3-fg]quinoline-7-carboxylic acid phenylamide. MS: 461 (M+H)$^+$

EXAMPLE 73

(6aR,9R)-5-Iodo-9-(pyrrolidine-1-carbonyl)-6,6a,8,9-tetrahydro-4H-indolo[4,3-fg]quinoline-7-carboxylic acid phenylamide (6aR,9R)-5-Iodo-9-(pyrrolidine-1-carbonyl)-6,6a,8,9-tetrahydro-4H-indolo[4,3-fg]quinoline-7-carboxylic acid phenylamide is prepared following a similar procedure as described for Example 72 using N-iodosuccinimide instead of N-chlorosuccinimide. MS: 553 (M+H)$^+$

EXAMPLE 74

(6aR,9R)-5-Bromo-9-(pyrrolidine-1-carbonyl)-6,6a,8,9-tetrahydro-4H-indolo[4,3-fg]quinoline-7-carboxylic acid phenylamide Step 1: (6aR,9R)-5-Bromo-7-methyl-4,6,6a,7,8,9-hexahydro-indolo[4,3-fg]quinoline-9-carboxylic acid Lysergic acid (8.05 g, 30 mmol) is suspended in dioxane and is treated with dropwise addition of TFA (exothermic). Bromine (1.54 ml, 30 mmol, 1.0 eq.) in chloroform is added dropwise. The reaction is cooled to 5° C. and product crystallizes. (6aR,9R)-5-Bromo-7-methyl-4,6,6a,7,8,9-hexahydro-indolo[4,3-fg]quinoline-9-carboxylic acid is isolated by filtration and re-crystallised from diethylether. Rf=0.5, 10% MeOH:DCM, M+H$^+$=346, 348, m.p.>245 (decomposition).

Step 2: (6aR,9R)-5-Bromo-7-methyl-4,6,6a,7,8,9-hexahydro-indolo[4,3-fg]quinolin-9-yl)-pyrrolidin-1-yl-methanone To a 50 ml round-bottom flask containing (6aR,9R)-5-bromo-7-methyl-4,6,6a,7,8,9-hexahydro-indolo[4,3-fg]quinoline-9-carboxylic acid (5.0 g, 13.38 mmol) in DMF (20 ml) is added HATU (6.10 g, 16.06 mmol, 1.2 eq.) and the reaction mixture stirred for 1 hour at room temperature. Pyrrolidine (2.24 ml, 26.78 mmol, 2.0 eq.) is added and the reaction mixture is stirred for a further 2 hours at room temperature. TLC in 10% methanol/DCM shows complete conversion of starting material (visualized by Chlorine/TBDM reagent and by UV). 4M HCl (150 ml) and water (150 ml) are added to the reaction mixture and ethyl acetate (200 ml) added. Following extraction, the aqueous phase is re-extracted with ethyl acetate (2×200 ml) and the combined extracts washed with sat. bicarbonate (2×200 ml), water (200 ml), sat. brine (200 ml), filtered (at the pump), dried (MgSO$_4$) and concentrated in vacuo to give a dark brown oil. Purification is carried out by Normal Phase Flash column chromatography (Biotage Flash 40, 90 g cartridge) using 20% ethyl acetate/hexane ramped to 100% ethyl acetate and then to 5% methanol/ethyl acetate over 5 litres. The relevant fractions are combined, concentrated in vacuo and left in a high vac oven for 3 hrs at 50° C. to give a mixture of (6aR,9R)-5-Bromo-7-methyl-4,6,6a,7,8,9-hexahydro-indolo[4,3-fg]quinoline-9-carboxylic acid and a diastereomer.

Step 3: ((R)-5-Bromo-7-methyl-7-oxy-4,6,6a,7,8,9-hexahydro-indolo[4,3-fg]quinolin-9-yl)-pyrrolidin-1-yl-methanone 1.19 (2.75 mmol) of the product from step 2 is dissolved in THF (40 ml) with an ultrasonicator and then the solution chilled to −40° C. using an acetone/dry ice bath. m-CPBA (0.640 g, 3.75 mmol, 1.35 eq.) is added portionwise (over 30 minutes) and the resulting dark-brown coloured reaction mixture allowed to warm to 0° C. with constant stirring (approx. 1.5 hours). A solution of Iron (II) chloride (0.174 g, 1.37 mmol, 0.5 eq.) in water (10 ml) is added dropwise to the reaction mixture at 0° C. After 1 hour the RM is allowed to slowly warm to room temperature and then stirring continued for 2 hours. TLC in 20% methanol/DCM showed complete consumption of N-Oxide intermediate. A solution of sodium bisulphite (1 g) in water (5 ml) is added to the reaction mixture and then the volatiles are removed in vacuo to give a black foam. This is purified on the Biotage Flash 40 system using 2% methanol/DCM ramped to 8% methanol/DCM in 2% increments per litre of solvent providing ((R)-5-Bromo-7-methyl-7-oxy-4,6,6a,7,8,9-hexahydro-indolo[4,3-fg]quinolin-9-yl)-pyrrolidin-1-yl-methanone.

Step 4: (6aR,9R)-5-Bromo-9-(pyrrolidine-1-carbonyl)-6,6a,8,9-tetrahydro-4H-indolo[4,3-fg]quinoline-7-carboxylic acid phenylamide The product from step 3 (0.504 g, 1.32 mmol) is dissolved in anhydrous dichloromethane (20 ml) and the solution cooled to 0° C. with an ice-salt bath. Hünigs base (0.940 ml, 0.21 mmol) and phenylisocyanate (0.388 ml, 3.9 mmol) are then added and the reaction mixture is allowed to warm to room temperature. Stirring is continued for 16 hours. TLC in 20% methanol/DCM shows complete consumption of starting material. Purification is carried out by Normal Phase Flash column chromatography (Biotage Flash 40, 40 g cartridge) using a gradient system starting with 20% ethyl acetate/hexane (1 Ltr) ramped to 30% Ethyl acetate/hexane (1 Ltr), then 50% ethyl acetate/hexane (1 Ltr) and finally 60% Ethyl acetate/hexane (1 Ltr). The relevant fractions are combined, concentrated in vacuo and left in a high vac oven for 3 hrs at 50° C. (6aR,9R)-5-Bromo-9-(pyrrolidine-1-carbonyl)-6,6a,8,9-tetrahydro-4H-indolo[4,3-fg]quinoline-7-carboxylic acid phenylamide β is isolated as a colorless solid. MS/ES: 505 (M+H)$^+$

EXAMPLE 75

(6aR,9R)-5-Phenyl-9-(pyrrolidine-1-carbonyl)-6,6a,8,9-tetrahydro-4H-indolo[4,3-fg]quinoline-7-carboxylic acid phenylamide To a 5 ml Microwave reaction vial containing Example 74 (0.05 g, 0.27 mmol) in DME (1 ml) is added phenylboronic acid (46 mg, 0.37 mmol, 1.4 eq.) and 2M sodium carbonate (1.50 ml). The reaction mixture is purged with nitrogen for 5 minutes whilst stirring and then the catalyst (30 mg) added. The walls of the vial are washed with nitrogen-flushed ethanol (0.75 ml) and the reaction mixture is left purging with nitrogen for another 5 minutes. The vial is sealed with a cap and the reaction mixture run on the Microwave at 100° C. for 300 seconds (fixed hold time). TLC in 10% methanol/DCM shows total consumption of starting material (visualized by Chlorine/TBDM reagent and by UV). The reaction mixture is partitioned between sat. bicarbonate (20 ml) and dichloromethane (20 ml). The organics are applied directly to a Flash column and purified by Normal Phase Flash column chromatography (Biotage Flash 40, 40 g cartridge) using 30% ethyl acetate/hexane (1 Ltr) ramped to 40% ethyl acetate/hexane (1 Ltr) as the solvent. The relevant fractions are combined, concentrated in vacuo and left in a high vac oven for 3 hrs at 50° C. and product is isolated MS: 503 (M+H)$^+$ The compounds of formula

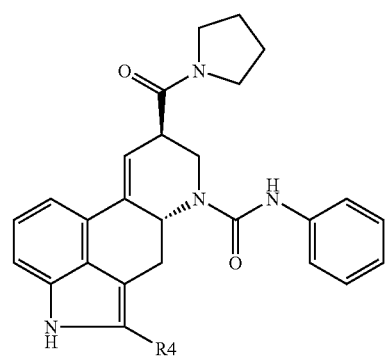

wherein R$_4$ has the significances given in Table 5, are prepared using similar procedures.

TABLE 5

| Ex. | R$_4$ | MS (ES$^+$) |
|---|---|---|
| 76 | | 528 |
| 77 | | 534 |

EXAMPLE 78

(6aR,9R)-5-(3-Hydroxy-prop-1-ynyl)-9-(pyrrolidine-1-carbonyl)-6,6a,8,9-tetrahydro-4H-indolo[4,3-fg]quinoline-7-carboxylic acid To a 5 ml Microwave reaction vial containing a solution of example 74 (50 mg, 0.1 mmol), triphenylphosphine (3 mg, 0.001 mmol, 0.1 eq.), copper iodide (1 mg, 0.005 mmol, 0.05 eq.), triethylamine (1 ml), pyridine (1 ml) is added propargyl alcohol (0.007 ml, 0.12 mmol, 1.2 eq.) and the reaction mixture is purged with nitrogen for 5 minutes whilst stirring. The dichlorobis(triphenylphosphine) palladium catalyst (7 mg, 0.01 mmol, 0.1 eq.) is added and the reaction left purging with nitrogen for another 5 minutes. The vial is sealed with a cap and the RM run on the Microwave at 100° C. for 300 seconds (fixed hold time). LC-MS shows some conversion to product. Catalyst (7 mg, 0.01 mmol, 0.1 eq.), propargyl alcohol (7 μl, 0.12 mmol, 1.2 eq.) and copper (I) iodide (1 mg, 0.005 mmol, 0.05 eq.), are added to the reaction mixture and run in the microwave for another 300 s at 100° C. LC-MS shows approx 1:1 conversion of starting material:product. The reaction mixture is run for another 600 s at 100° C. after which time LC-MS shows virtual consumption of starting material to product. Purification is carried out by Normal Phase Flash column chromatography (Biotage Flash 40, 40 g cartridge) using 50% ethyl acetate/hexane (2 Ltr). The relevant fractions are combined, concentrated in vacuo and dried in a high vacuum oven for 3 hrs at 50° C. and the resulting product is isolated. MS/ES: 481 (M+H)+

EXAMPLE 79

[(6aR,9R)-7-Phenylcarbamoyl-9-(pyrrolidine-1-carbonyl)-6a,7,8,9-tetrahydro-6H-indolo[4,3-fg]quinolin-4-yl]-acetic acid isopropyl ester 5 g (11.72 mmol) of Example 13 is dissolved in 100 ml of dichloromethane. At room temperature 30 ml 40% aqueous sodium hydroxide solution is added as well as 400 mg benzyltriethyl-ammoniumchloide. The reaction mixture is cooled to 0-5° C. and 6.23 ml (46.89 mmol, 4 eq.) isopropylbromoacetate is added and stirred for 1 hour. The reaction mixture is poured on ice and extracted with $CH_2Cl_2$, the organic layer is washed with water, dried with Na2SO4 and evaporated. The residue is purified by chromatography on silica eluting with tert.butyl-methyl ether to give [(6aR,9R)-7-Phenylcarbamoyl-9-(pyrrolidine-1-carbonyl)-6a,7,8,9-tetrahydro-6H-indolo[4,3-fg]quinolin-4-yl]-acetic acid isopropyl ester. MS/ES: 527 (M+H)+

EXAMPLE 80

[(6aR,9R)-7-Phenylcarbamoyl-9-(pyrrolidine-1-carbonyl)-6a,7,8,9-tetrahydro-6H-indolo[4,3-fg]quinolin-4-yl]-acetic acid

[(6aR,9R)-7-Phenylcarbamoyl-9-(pyrrolidine-1-carbonyl)-6a,7,8,9-tetrahydro-6H-indolo[4,3-fg]quinolin-4-yl]-acetic acid is isolated as a byproduct from the synthesis of Example 79. MS/ES: 485 (M+H)+

The compounds of formula

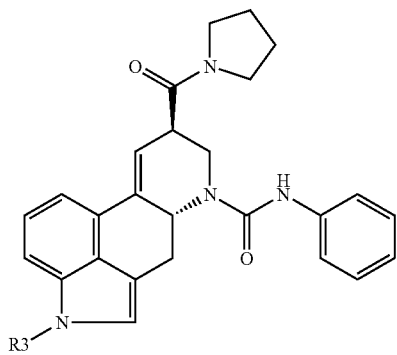

wherein $R_3$ has the significances given in Table 6, are prepared following a procedure similarly to Example 79.

TABLE 6

| Ex. | $R_3$ | MS (M + H) |
|---|---|---|
| 81 | ![structure] | 567 |
| 82 | ![structure] | 554 |
| 83 | ![structure] | 512 |
| 84 | ![structure] | 518 |

The compounds of formula

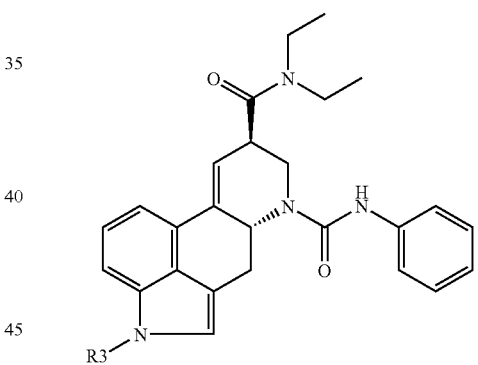

wherein $R_3$ has the significances given in Table 7, are prepared according to a procedure similar to Example 79 starting from Example 1 instead of Example 13 and using appropriate alkyl halides.

TABLE 7

| Ex. | $R_3$ | MS (M + H) |
|---|---|---|
| 85 | ![structure] | 519 |
| 86 | —$CH_3$ | 443 |

EXAMPLE 87

(6aR,9R)-4-(2-Hydroxy-ethyl)-9-(pyrrolidine-1-carbonyl)-6,6a,8,9-tetrahydro-4H-indolo[4,3-fg]quinoline-7-carboxylic acid phenylamide 3.99 g (7.57 mmol) of Ex.79 is dissolved in 100 ml tetrahydrofurane and at 0-5° C. 989 mg (45.43 mmol, 4 eq.) lithiumborhydride is added. The reaction mixture is stirred at room temperature for 4.5 hours. Then the reaction mixture is poured onto ice/acetic acid mixture (vigorous CO2 evolution) and extracted with dichloromethane. The organic layer is washed with water, dried with $Na_2SO_4$ and evaporated. The residue is purified by chromatography on silica eluting with dichloromethane:methanol 95:5 to give in the order of elution the desired β-isomer (6aR,9R)-4-(2-Hydroxy-ethyl)-9-(pyrrolidine-1-carbonyl)-6,6a,8,9-tetrahydro-4H-indolo[4,3-fg]quinoline-7-carboxylic acid phenylamide. MS/ES: 471 $(M+H)^+$

EXAMPLE 88

(6aR,9R)-4-(2-Morpholin-4-yl-ethyl)-9-(pyrrolidine-1-carbonyl)-6,6a,8,9-tetrahydro-4H-indolo[4,3-fg]quinoline-7-carboxylic acid phenylamide Step 1: Toluene-4-sulfonic acid 2-[(6aR,9R)-7-phenylcarbamoyl-9-(pyrrolidine-1-carbonyl)-6a,7,8,9-tetrahydro-6H-indolo[4,3-fg]quinolin-4-yl]-ethyl ester 1.12 g (2.38 mmol) of Example 87 is dissolved in 40 ml dichloromethane and at room temperature 437 mg (3.58 mmol, 1.5 eq.) dimethylaminopyridine is added and the mixture is cooled to 0-5° C. 683 mg (3.589 mmol, 1.5 eq.) 4-Methyl-benzenesulfonyl chloride is added and the reaction mixture is stirred at room temperature for 3.5 hours. The reaction mixture is poured onto ice and some 6 N sulfuric acid and extracted with dichloromethane. The organic layer is dried with Na2SO4 and evaporated. The residue is purified by chromatography on silica to give toluene-4-sulfonic add 2-[(6aR,9R)-7-phenylcarbamoyl-9-(pyrrolidine-1-carbonyl)-6a,7,8,9-tetrahydro-6H-indolo[4,3-fg]quinolin-4-yl]-ethyl ester.

Step 2: (6aR,9R)-4-(2-Morpholin-4-yl-ethyl)-9-(pyrrolidine-1-carbonyl)-6,6a,8,9-tetrahydro-4H-indolo[4,3-fg]quinoline-7-carboxylic acid phenylamide 80 mg (0.128 mmol) of the product of step 1 and 1 ml morpholine are stirred at room temperature for 16 hours. The reaction mixture is purified by chromatography on silica gel eluting with acetone:cyclohexane 6:4 to give (6aR,9R)-4-(2-Morpholin-4-yl-ethyl)-9-(pyrrolidine-1-carbonyl)-6,6a,8,9-tetrahydro-4H-indolo[4,3-fg]quinoline-7-carboxylic acid phenylamide. MS/ES: 540 $(M+H)^+$ The compounds of formula

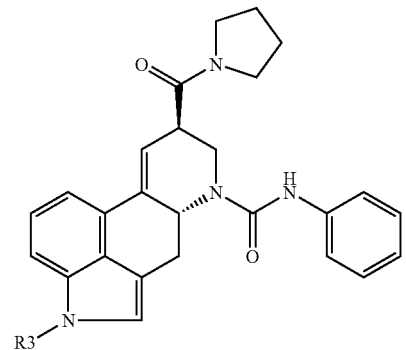

wherein $R_3$ has the significances given in Table 8, are prepared following a procedure similar to step 2 of Example 88.

TABLE 8

| Ex. | $R_3$ | MS (M + H) |
|---|---|---|
| 89 | | 498 |
| 90 | | 524 |
| 91 | | 540 |
| 92 | | 556 |
| 93 | | 538 |
| 94 | | 554 |
| 95 | | 539 |

TABLE 8-continued

| Ex. | R₃ | MS (M + H) |
|---|---|---|
| 96 | (structure: -CH₂CH₂-piperazine-) | 553 |

EXAMPLE 97

(6aR,9R)-4-Acetyl-9-(pyrrolidine-1-carbonyl)-6,6a,8,9-tetrahydro-4H-indolo[4,3-fg]quinoline-7-carboxylic acid phenylamide 80 mg of Example 13 (0.18 mmol) and 69 mg (0.56 mmol, 3 eq.) dimethylaminopyrimidine are dissolved in 3 ml dichloroethane and 0.036 ml (0.37 mmol, 2 eq.) acetic anhydride is added. The reaction mixture is stirred and 65° C. for 4 hours. The reaction mixture is separated between dichloromethane and saturated aqueous bicarbonate solution. The organic layer is dried with Na2SO4 and evaporated. The crude product is purified by chromatography on silica eluting with dichloromethane:methanol 97:3 to give (6aR,9R)-4-acetyl-9-(pyrrolidine-1-carbonyl)-6,6a,8,9-tetrahydro-4H-indolo[4,3-fg]quinoline-7-carboxylic acid phenylamide. MS/ES: 469 (M+H)⁺

EXAMPLE 98

(6aR,9R)-4-Hydroxy-9-(pyrrolidine-1-carbonyl)-6,6a,8,9-tetrahydro-4H-indolo[4,3-fg]quinoline-7-carboxylic acid phenylamide Step 1: (5aS,6aR,9R)-9-(Pyrrolidine-1-carbonyl)-5,5a,6,6a,8,9-hexahydro-4H-indolo[4,3-fg]quinoline-7-carboxylic acid phenylamide 351 mg (0.82 mmol) of Ex. 13 is dissolved in 6 ml trifluoroacetic acid and 0.407 ml (2.47 mmol, 3 eq.) triethylsilane is added. The reaction mixture is stirred at room temperature for 1 hour and 10 minutes. Then the reaction mixture is separated between ethyl acetate and saturated aqueous bicarbonate solution, the organic layer is washed with brine, dried with Na2SO4 and evaporated and crystallized from tert. butyl methyl ether to give (5aS,6aR,9R)-9-(Pyrrolidine-1-carbonyl)-5,5a,6,6a,8,9-hexahydro-4H-indolo[4,3-fg]quinoline-7-carboxylic acid phenylamide Step 2: (6aR,9R)-4-Hydroxy-9-(pyrrolidine-1-carbonyl)-6,6a,8,9-tetrahydro-4H-indolo[4,3-fg]quinoline-7-carboxylic acid phenylamide 212 mg (0.49 mmol) of the product of step 1 is dissolved in 12 ml methanol and 41 mg (0.12 mmol, 0.25 eq.) sodium wolframate dehydrate in some drops of water is added. Then 670 μl 30% H2O2 (10 eq.) is added at 0° C. and stirred at room temperature for 50 minutes. The reaction mixture is separated with dichloromethane and saturated aqueous bicarbonate solution, the organic layer is washed with brine, dried with Na2SO4 and evaporated and purified by chromatography on silica eluting with tert. butyl methyl ether:cyclohexane 9:1 to give (6aR,9R)-4-Hydroxy-9-(pyrrolidine-1-carbonyl)-6,6a,8,9-tetrahydro-4H-indolo[4,3-fg]quinoline-7-carboxylic acid phenylamide. MS/ES: 441 (M+H)⁺

EXAMPLE 99

(6aR,9R)-4-Methoxy-9-(pyrrolidine-1-carbonyl)-6,6a,8,9-tetrahydro-4H-indolo[4,3-fg]quinoline-7-carboxylic acid phenylamide 17 mg (0.038 mmol) of Example 98 is dissolved in 2 ml methanol:dichloromethane 1:1 and freshly prepared diazomethane solution is distilled into the reaction mixture for 10 minutes until the yellow colour persisted. The reaction mixture is evaporated and purified by chromatography on silica using tert. butyl methyl ether:cyclohexane 9:1 as eluent. The product crystallizes upon evaporation to give (6aR,9R)-4-Methoxy-9-(pyrrolidine-1-carbonyl)-6,6a,8,9-tetrahydro-4H-indolo[4,3-fg]quinoline-7-carboxylic acid phenylamide. MS/ES: 458 (M+H)⁺

The compounds of formula I in free form or in pharmaceutically acceptable salt form exhibit valuable pharmacological properties, e.g. as CXCR3 antagonists, e.g. as indicated in in vitro tests and therefore indicated for therapy.

a) CXCR3 Membrane Binding Assay

A ligand binding assay is used to identify inhibitors of I-TAC binding to CXCR3 expressing membranes. Cell membranes are prepared from CHO cells transfected with human CXCR3. The binding of the $^{125}$I labeled CXCR3 ligand e.g. I-TAC (CXCL11) to CXCR3 is assessed using the Scintillation Proximity Assay (SPA) technology (Amersham Pharmacia Biotech). Buffer or serial dilutions of compound are incubated for 2 hours at room temperature with labeled CXCR3 ligand (e.g. I-TAC), CXCR3 expressing membranes and WGA coated PVT beads. The plates are then centrifuged and counted in a Topcount (Packard) instrument. The data are reported as the concentration of compound required to achieve 50% inhibition of $^{125}$I ligand binding. In this assay, the compounds of formula I have an $IC_{50}$ value from 1 μM-1 nM. For example, the compounds of Examples 18, 23, 43, 59 and 79 nM have an $IC_{50}$ of 54, 61, 23, 43 and 145, respectively.

b) CXCR3 Functional Assay—$Ca^{2+}$ Mobilization

CXCR3 ligand-induced $Ca^{2+}$ mobilization is assessed in CXCR3 transfected L1.2 cells (a mouse pre B cell line). For this, cells are loaded with the $Ca^{2+}$-sensitive fluorochrome Fluo-4 (Molecular Probes). After washing, the cells are pre-incubated with low molecular weight inhibitors for 2 h at room temperature. The transient increase in intracellular $Ca^{2+}$ after the addition of the CXCR3 ligand (e.g. I-TAC) is monitored in a fluorescence image plate reader (FLIPR) instrument. The inhibition of CXCR3 ligand induced $Ca^{2+}$ mobilization in the presence of CXCR3 antagonists is reported as $IC_{50}$ values i.e. the concentration of compound which reduces the maximal $Ca^{2+}$ response to 50%. In this assay, the compounds of formula I have an $IC_{50}$ value from 1 μM-1 nM. For example, the compounds of Examples 18, 23, 43, 59 and 79 have an $IC_{50}$ of 18, 8, 16, 20 and 53 nM, respectively.

c) CXCR3 Functional Assay—Chemotaxis

The directed cell migration induced by CXCR3 ligands e.g. I-TAC is assessed using 96-well disposable chemotaxis chambers (Multiscreen MIC, Costar) with polycarbonate membranes containing pores of 5 μm diameter. Chemokine (e.g. I-TAC) is placed in the bottom well of the chamber and cells (e.g. CXCR3 transfected L-1.2 cells) are placed in the top compartment of the chemotaxis chamber. Cell migration across the porous membrane is allowed for 4 h at 37° C. Cells migrated from the top compartment to the bottom compartment are quantified by flow cytometry. When LMW inhibitors are tested, compounds are added to both compartments at the identical concentrations; Serial dilutions of compounds are tested to assess their inhibitory effect on CXCR3 dependent cell migration. The concentration of LMW CXCR3 inhibitors which leads to a reduction of migrated cells by 50% is reported as $IC_{50}$. In this assay, the compounds of formula I have an $IC_{50}$ value from 1 μM-1 nM. For example, the compounds of Examples 18 and 43 have an $IC_{50}$ of 74 and 75 nM, respectively.

d) Experiments performed in murine animal models show that vessel wall remodeling after experimental injury (e.g. induced by allotransplantation) is significantly reduced in the absence of functional CXCR3.

The compounds of formula I are, therefore, useful in the prevention and/or treatment of diseases or disorders mediated by interactions between chemokine receptors, e.g. CXCR3, and their ligands, e.g. in autoimmune diseases, e.g. rheumatoid arthritis, systemic lupus erythematosus, Hashimoto's thyroiditis, multiple sclerosis, myasthenia gravis, diabetes type I or II and the disorders associated therewith, vasculitis, pernicious anemia, Sjoegren syndrome, uveitis, psoriasis, alopecia greata and others, allergic diseases, e.g. allergic asthma, atopic dermatitis, allergic rhinitis/conjunctivitis, allergic contact dermatitis, inflammatory diseases optionally with underlying aberrant reactions, e.g. inflammatory bowel disease, Crohn's disease or ulcerative colitis, intrinsic asthma, inflammatory lung injury, inflammatory liver injury, inflammatory glomerular injury, atherosclerosis, osteoarthritis, irritant contact dermatitis and further eczematous dermatites, seborrhoeic dermatitis, cutaneous manifestations of immunologically-mediated disorders, inflammatory eye disease, keratoconjunctivitis, myocarditis or hepatitis, ischemia/reperfusion injury, e.g. myocardial infarction, stroke, gut ischemia, renal failure or hemorrhage shock, traumatic shock and others, cancer, e.g. solid tumors or lymphatic cancer such as T cell lymphomas or T cell leukemias, metastasizing or angiogenesis, infectious diseases, e.g. toxic shock (e.g. superantigen induced), septic shock, adult respiratory distress syndrome, or transplantation, such as acute or chronic rejection of organ, tissue or cell allo- or xenografts or delayed graft function. By transplantation is meant allo- or xeno grafts of e.g. cells, tissues or solid organs, for example pancreatic islets, stem cells, bone marrow, corneal tissue, neuronal tissue, heart, lung, combined heart-lung, kidney, liver, bowel, pancreas, trachea or esophagus. Chronic rejection is also named graft vessel diseases.

For the above uses the required dosage will of course vary depending on the mode of administration, the particular condition to be treated and the effect desired. In general, satisfactory results are indicated to be obtained systemically at daily dosages of from about 0.01 to 10 mg/kg per body weight. An indicated daily dosage in the larger mammal, e.g. humans, is in the range from about 0.5 mg to about 1000 mg, conveniently administered, for example, in divided doses up to four times a day or in retard form. Suitable unit dosage forms for oral administration comprise from ca. 1 to 500 mg active ingredient.

The compounds of formula I may be administered by any conventional route, in particular enterally, e.g. orally, e.g. in the form of tablets or capsules, or parenterally, e.g. in the form of injectable solutions or suspensions, topically, e.g. in the form of lotions, gels, ointments or creams, or in a nasal or a suppository form. Pharmaceutical compositions comprising a compound of formula I in free form or in pharmaceutically acceptable salt form in association with at least one pharmaceutical acceptable carrier or diluent may be manufactured in conventional manner by mixing with a pharmaceutically acceptable carrier or diluent.

The compounds of formula I may be administered in free form or in pharmaceutically acceptable salt form e.g. as indicated above. Such salts may be prepared in conventional manner and exhibit the same order of activity as the free compounds.

In accordance with the foregoing the present invention further provides:

1.1 A method for preventing or treating disorders or diseases mediated by interactions between chemokine receptors and their ligands, e.g. such as indicated above, in a subject in need of such treatment, which method comprises administering to said subject an effective amount of a compound of formula I or a pharmaceutically acceptable salt thereof;

1.2 A method for preventing or treating inflammatory or autoimmune diseases, e.g. as indicated above, in a subject in need of such treatment, which method comprises administering to said subject an effective amount of a compound of formula I or a pharmaceutically acceptable salt thereof;

2. A compound of formula I or a pharmaceutically acceptable salt thereof for use as a pharmaceutical, e.g. in any of the methods as indicated under 1.1 or 1.2 above.

3. A pharmaceutical composition, e.g. for use in any of the methods as in 1.1 or 1.2 above comprising a compound of formula I or a pharmaceutically acceptable salt thereof in association with a pharmaceutically acceptable diluent or carrier therefor.

4. A compound of formula I or a pharmaceutically acceptable salt thereof for use in the preparation of a pharmaceutical composition for use in any of the method as in 1.1 or 1.2 above.

The compounds of formula I may be administered as the sole active ingredient or in conjunction with, e.g. as an adjuvant to, other drugs e.g. in immunosuppressive or immunomodulating regimens or other anti-inflammatory agents, e.g. for the treatment or prevention of allo- or xenograft acute or chronic rejection or inflammatory or autoimmune disorders, a chemotherapeutic agent or an anti-infective agent, e.g. an anti-viral agent such as e.g. an anti-retroviral agent or an antibiotic. For example, the compounds of formula I may be used in combination with a calcineurin inhibitor, e.g. cyclosporin A or FK 506; a mTOR inhibitor, e.g. rapamycin, 40-O-(2-hydroxyethyl)-rapamycin, CC1779, ABT578 or a rapalog, e.g. AP23573, AP23464, AP23675, AP23841, TAFA-93, biolimus 7 or biolimus 9; an ascomycin having immunosuppressive properties, e.g. ABT-281, ASM981, etc.; corticosteroids; cyclophosphamide; azathioprine; methotrexate; leflunomide; mizoribine; mycophenolic acid; mycophenolate mofetil; 15-deoxyspergualine or an immunosuppressive homologue, analogue or derivative thereof; a SI P receptor agonist or modulator, e.g. FTY720 or an analogue thereof; a PKC inhibitor, e.g. as disclosed in WO 02/38561 or WO 03/82859, e.g. the compound of Example 56 or 70; monoclonal antibodies to leukocyte receptors, e.g., MHC, CD2, CD3, CD4, CD7, CD8, CD11a/CD18, CD25, CD27, CD28, CD40. CD45, CD52, CD58, CD80, CD86, CD137, ICOS, CD150 (SLAM), OX40, 4-1BB or to their ligands, e.g. CD154, or antagonists thereof; other immunomodulatory compounds, e.g. a recombinant binding molecule having at least a portion of the extracellular domain of CTLA4 or a mutant thereof, e.g. an at least extracellular portion of CTLA4 or a mutant thereof joined to a non-CTLA4 protein sequence, e.g. CTLA4Ig (for ex. designated ATCC 68629) or a mutant thereof, e.g. LEA29Y; adhesion molecule inhibitors, e.g. LFA-1 antagonists, ICAM-1 or -3 antagonists, VCAM4 antagonists or VLA4 antagonists; or antichemokine antibodies, e.g. anti MCP-1 antibodies, or antichemokine receptor antibodies or low molecular weight chemokine receptor antagonists.

Where the compounds of formula I are administered in conjunction with other immunosuppressive/immunomodulatory, anti-inflammatory or chemotherapeutic therapy, dosages of the co-administered immunosuppressant, immunomodulatory, anti-inflammatory or chemotherapeutic compound will of course vary depending on the type of co-drug employed, e.g. whether it is a steroid or a calcineurin inhibitor, on the specific drug employed, on the condition being treated and so forth.

In accordance with the foregoing the present invention provides in a yet further aspect:

5. A method as defined above comprising co-administration, e.g. concomitantly or in sequence, of a therapeutically effective amount of a compound of formula I and at least a second drug substance, e.g. an immunosuppressant, immunomodulatory, anti-inflammatory, anti-infective or chemotherapeutic drug, e.g. as indicated above.

6. A pharmaceutical combination, e.g. a kit, comprising a) a first agent which is a CXCR3 antagonist, e.g. a compound of formula I as disclosed herein, in free form or in pharmaceutically acceptable salt form, and b) at least one co-agent, e.g. an immunosuppressant, immunomodulatory, anti-inflammatory, anti-infective or chemotherapeutic drug. The kit may comprise instructions for its administration.

The terms "co-administration" or "combined administration" or the like as utilized herein are meant to encompass administration of the selected therapeutic agents to a single patient, and are intended to include treatment regimens in which the agents are not necessarily administered by the same route of administration or at the same time.

The term "pharmaceutical combination" as used herein means a product that results from the mixing or combining of more than one active ingredient and includes both fixed and non-fixed combinations of the active ingredients. The term "fixed combination" means that the active ingredients, e.g. a compound of formula I and a co-agent, are both administered to a patient simultaneously in the form of a single entity or dosage. The term "non-fixed combination" means that the active ingredients, e.g. a compound of formula I and a co-agent, are both administered to a patient as separate entities either simultaneously, concurrently or sequentially with no specific time limits, wherein such administration provides therapeutically effective levels of the 2 compounds in the body of the patient. The latter also applies to cocktail therapy, e.g. the administration of 3 or more active ingredients.

The invention claimed is:
1. A compound of formula I

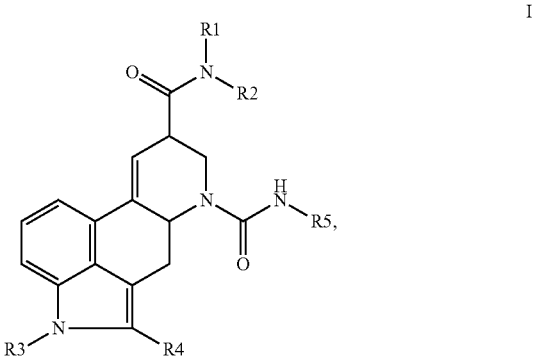

wherein
either each of $R_1$ and $R_2$, independently, is H; optionally $R_{10}$- and/or $R_{11}$-substituted phenyl; optionally $R_{10}$- and/or $R_{11}$-substituted phenyl-$C_1$-$C_4$-alkyl; optionally $R_{10}$- and/or $R_{11}$-substituted heteroaryl-$C_1$-$C_4$-alkyl; optionally $R_{10}$- and/or $R_{11}$-substituted heteroaryl N-oxide; optionally $R_{10}$-substituted $C_1$-$C_8$-alkyl; optionally $R_{10}$-substituted $C_2$-$C_8$-alkenyl; optionally $R_{10}$-substituted $C_2$-$C_8$-alkynyl; optionally $R_{10}$-substituted $C_3$-$C_8$-cycloalkyl; or optionally $R_{10}$-substituted $C_4$-$C_8$-cycloalkenyl;
or $R_1$ and $R_2$ form, together with the nitrogen atom to which they are attached, an optionally $R_{10}$-substituted 3-8-membered ring containing, in addition to the nitrogen atom, up to 2 other heteroatoms selected independently from N, O and S;
where $R_{10}$ represents 1-to-4 substituents independently selected from $C_1$-$C_6$-alkyl; $C_1$-$C_6$-hydroxyalkyl; $C_1$-$C_6$-alkoxyalkyl; $C_1$-$C_6$-halogenoalkyl; $C_3$-$C_6$-cycloalkyl; $C_2$-$C_6$-alkenyl; $C_3$-$C_6$-cycloalkenyl; $C_2$-$C_6$-alkynyl; phenyl; heteroaryl; heteroaryl N-oxide; F; Cl; Br; I; OH; $OR_9$; $OCOR_9$; $OCOOR_9$; $OCONHR_9$; $OCONR_9R_9$; $OSO_2R_9$; $COR_9$; COOH; $COOR_9$; $CONH_2$; $CONHR_9$; $CONR_9R_9$; $CF_3$; $CHF_2$; $CH_2F$; $C_1$-$C_4$-alkyl$NH_2$; $C_1$-$C_4$-alkyl$NHR_9$; $C_1$-$C_4$-alkyl$NR_9R_9$; CN; $NO_2$; $NH_2$; $NHR_9$; $NR_9R_9$; $NHCOR_9$; $NR_9COR_9$; $NHCONHR_9$; $NHCONH_2$; $NR_9CONHR_9$; $NR_9CONR_9R_9$; $NHCOOR_9$; $NR_9COOR_9$; $NHSO_2R_9$; $N(SO_2R_9)_2$; $NR_9SO_2R_9$; $SR_9$; $SOR_9$; $SO_2R_9$; $SO_2NH_2$; $SO_2NHR_9$; $SO_2NR_9R_9$;
or $R_{10}$ is =O attached to a carbon atom of phenyl or heteroaryl, or may be one or two =O's attached to the same S atom of heteroaryl, if any;
$R_{11}$ represents two adjacent substituents which form an annulated 4-7-membered nonaromatic ring optionally containing up to two heteroatoms selected independently from N, O and S; and
each $R_9$, independently, is $C_1$-$C_6$-alkyl; hydroxyl-$C_1$-$C_6$-alkyl; $C_3$-$C_6$-cycloalkyl; $C_2$-$C_6$-alkenyl; $C_2$-$C_6$-alkynyl; phenyl; benzyl; heteroaryl; —$CH_2$-heteroaryl; or $CF_3$; or two $R_9$'s, together with the N-atom to which they are attached, form an optionally $R_{10}$-substituted 4-8-membered ring containing, in addition to the N-atom, up to 2 other heteroatoms selected independently from N, O and S;
$R_3$ is H; $OR_1$; $CH_2R_1R_2$; $CH_2NR_1R_2$; $(CH_2)_2NR_1R_2$; $CH_2$—$CH_2$—$OR_1$; $CH_2$—CO—$NR_1R_2$; or CO—$CH_2R_1R_2$;

$R_4$ is F; Cl; Br; I; $OR_1$; $NR_1R_2$; H; optionally $R_{10}$- and/or $R_{11}$-substituted phenyl; optionally $R_{10}$- and/or $R_{11}$-substituted phenyl-$C_1$-$C_4$-alkyl; optionally $R_{10}$- and/or $R_{11}$-substituted heteroaryl; optionally $R_{10}$- and/or $R_{11}$-substituted heteroaryl-$C_1$-$C_4$-alkyl; optionally $R_{10}$- and/or $R_{11}$-substituted heteroaryl N-oxide; optionally $R_{10}$-substituted $C_1$-$C_8$-alkyl; optionally $R_{10}$-substituted $C_2$-$C_8$-alkenyl; optionally $R_{10}$-substituted $C_2$-$C_8$-alkynyl; optionally $R_{10}$-substituted $C_3$-$C_8$-cycloalkyl; or optionally $R_{10}$-substituted $C_4$-$C_8$-cycloalkenyl; and $R_5$ is optionally $R_{10}$- and/or $R_{11}$-substituted phenyl; optionally $R_{10}$- and/or $R_{11}$-substituted phenyl-$C_1$-$C_4$-alkyl; optionally $R_{10}$- and/or $R_{11}$-substituted heteroaryl; optionally $R_{10}$-and/or $R_{11}$-substituted heteroaryl-$C_1$-$C_4$-alkyl; optionally $R_{10}$- and/or $R_{11}$-substituted heteroaryl N-oxide; optionally $R_{10}$-substituted $C_1$-$C_8$-alkyl; optionally $R_{10}$-substituted $C_2$-$C_8$-alkenyl; optionally $R_{10}$-substituted $C_2$-$C_8$-alkynyl; optionally $R_{10}$-substituted $C_3$-$C_8$-cycloalkyl; or optionally $R_{10}$-substituted $C_4$-$C_8$-cycloalkenyl, in free form or in salt form.

2. A process for the preparation of a compound of formula I according to claim 1, which process comprises a) for the preparation of a compound of formula I, wherein each of $R_3$ and $R_4$ is H, reacting a compound of formula II

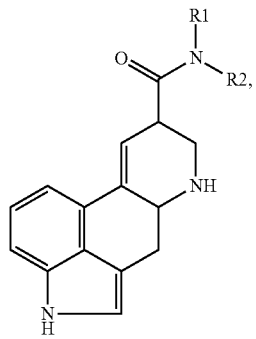

wherein $R_1$ and $R_2$ are as defined in claim 1,
with a urea-forming agent selected from phosgene, triphosgene and trichloromethylformate, and an amine of the formula $R_5$—$NH_2$, where $R_5$ is as defined in claim 1; or b) for the preparation of a compound of formula I wherein each of $R_3$ and $R_4$ is H, amidating a compound of formula III

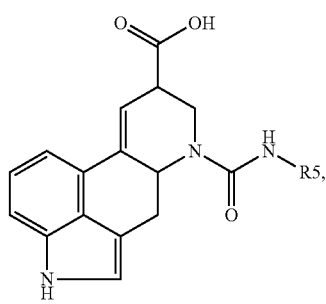

wherein $R_5$ is as defined in claim 1, or a carboxy-functional derivative thereof selected from an acid chloride, a mixed anhydride and a symmetrical anhydride, with an amine of the formula $R_1$—NH—$R_2$, where $R_1$ and $R_2$ are as defined in claim 1;

and, where required, converting the resulting compound of formula I obtained in free form into the desired salt form, or vice versa.

3. A pharmaceutical composition comprising a compound of formula I according to claim 1 or a pharmaceutically-acceptable salt thereof together with one or more pharmaceutically-acceptable diluents or carriers therefor.

4. A compound of the formula

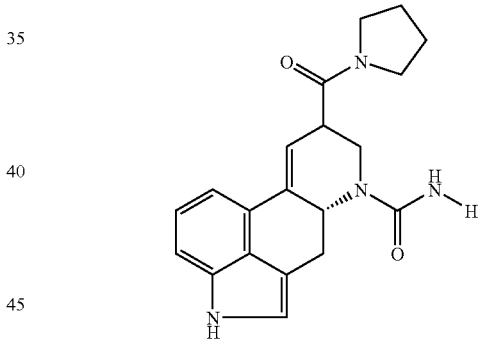

in free form or in salt form.

* * * * *